(12) United States Patent
Lewis et al.

(10) Patent No.: US 7,398,598 B2
(45) Date of Patent: *Jul. 15, 2008

(54) METHODS FOR MANUFACTURING ENDODONTIC INSTRUMENTS

(75) Inventors: Paul Lewis, Midvale, UT (US); Barry L. Hobson, Grantsville, UT (US); Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 205 days.

This patent is subject to a terminal disclaimer.

(21) Appl. No.: 10/991,178

(22) Filed: Nov. 17, 2004

(65) Prior Publication Data

US 2005/0069837 A1    Mar. 31, 2005

Related U.S. Application Data (63) Continuation-in-part of application No. 10/436,938, filed on May 13, 2003, now Pat. No. 6,968,619.

(51) Int. Cl.
*A61C 5/02* (2006.01)
*B23P 13/00* (2006.01)

(52) U.S. Cl. .................... 29/896.1; 433/102; 216/91

(58) Field of Classification Search ............... 29/896.1, 29/896.11; 433/102; 216/91
See application file for complete search history.

(56) References Cited

U.S. PATENT DOCUMENTS

| | | | |
|---|---|---|---|
| 1,372,170 A | | 3/1921 | Judd |
| 2,173,218 A | | 9/1939 | Zoppi .............................. 76/24 |
| 2,434,286 A | * | 1/1948 | Pfann .......................... 205/664 |
| 2,724,918 A | * | 11/1955 | Triman .................. 156/345.15 |
| 3,803,014 A | | 4/1974 | Atkinson .................... 204/206 |
| 3,823,514 A | | 7/1974 | Tsuchiya ..................... 51/281 |
| 3,869,373 A | | 3/1975 | Schacher et al. ............ 204/224 |
| 4,116,755 A | * | 9/1978 | Coggins et al. ............. 216/109 |
| 4,934,934 A | | 6/1990 | Arpaio, Jr. et al. .......... 433/102 |
| 5,382,319 A | | 1/1995 | Tumminaro, Jr. ........... 156/664 |
| 5,527,332 A | * | 6/1996 | Clement ..................... 606/171 |
| 5,653,590 A | | 8/1997 | Heath et al. ................. 433/102 |
| 5,741,429 A | | 4/1998 | Donadio, III et al. .......... 216/8 |
| 5,762,497 A | | 6/1998 | Heath .......................... 433/102 |
| 5,762,541 A | | 6/1998 | Heath et al. ................... 451/48 |
| 5,762,811 A | | 6/1998 | Munoz ........................ 216/11 |
| 5,882,198 A | * | 3/1999 | Taylor et al. ................ 433/102 |

(Continued)

FOREIGN PATENT DOCUMENTS

EP    0 119 714    9/1984

(Continued)

*Primary Examiner*—David P. Bryant
*Assistant Examiner*—Sarang Afzali
(74) *Attorney, Agent, or Firm*—Workman Nydegger (57) ABSTRACT

A method of manufacturing endodontic files involves a chemical milling process to yield endodontic files having a desired taper and/or degree of sharpness. The process involves the steps of (a) forming helical cutting edges in the cutting portion of the metallic rod; and (b) chemically milling the cutting portion of the rod so as to sharpen and/or taper the cutting portion. The rod may be formed of any desirable metallic material, for example stainless steel or a nickel-titanium alloy. The cutting edges may be formed by torsioning, cutting, grinding, machining, laser micromachining, or grit blasting.

20 Claims, 10 Drawing Sheets

U.S. PATENT DOCUMENTS

| | | | |
|---|---|---|---|
| 5,928,144 A | 7/1999 | Real | 600/378 |
| 5,941,760 A * | 8/1999 | Heath et al. | 451/46 |
| 5,984,679 A | 11/1999 | Farzin-Nia et al. | 433/102 |
| 6,086,773 A | 7/2000 | Dufresne et al. | 216/8 |
| 6,315,558 B1 | 11/2001 | Farzin-Nia et al. | 433/102 |
| 6,575,747 B1 * | 6/2003 | Riitano et al. | 433/102 |
| 6,793,838 B2 | 9/2004 | Hansen et al. | |
| 7,207,111 B2 * | 4/2007 | Aloise et al. | 29/896.11 |

FOREIGN PATENT DOCUMENTS

| | | |
|---|---|---|
| EP | 0118714 | 9/1984 |
| JP | 02002144154 | 5/2002 |

* cited by examiner

METHODS FOR MANUFACTURING ENDODONTIC INSTRUMENTS

CROSS-REFERENCE TO RELATED APPLICATIONS

This application is a continuation-in-part of U.S. application Ser. No. 10/436,938, filed May 13, 2003, now U.S. Pat. No. 6,968,619 the disclosure of which is hereby incorporated herein in its entirety.

BACKGROUND OF THE INVENTION

1. The Field of the Invention

The invention is in the field of endodontics and particularly to endodontic instruments for use in preparing root canals to receive a filling material such as gutta percha. More particularly, the invention is in the field of processes for manufacturing endodontic files.

2. The Relevant Technology

When a root canal of a living tooth becomes infected or abscessed, discomfort and, in many cases, severe pain can result. In the early days of dentistry the only solution was to pull the tooth. More recently, however, dental practitioners have learned to successfully remove the pulp material forming the nerve of the tooth that has become infected and, after careful preparation of the canal that contained the nerve material, refill the canal with an inert filling material, such as gutta percha, permitting a patient to retain the tooth.

In order to achieve a successful root canal restoration, the dental practitioner must carefully and, as completely as possible, remove the infected pulp material of the tooth to prevent continued or future infection of surrounding tissues. The removal process typically includes shaping of the root canal so that it can be effectively and successfully filled and sealed with an inert material to eliminate the possibility of further infection occurring within the cleaned and shaped root canal.

Cleaning and shaping the root canal in preparation to filling with a material such as gutta percha is achieved by the use of metal files that include cutting surfaces for removing tissue in the root canal. The cutting surfaces are typically formed by helical flutes formed in the file. One or more helical cutting surfaces may be provided, which may be axially spaced as desired.

Some existing endodontic instruments and manufacturing methods are described in U.S. Pat. No. 4,934,934, U.S. Pat. No. 5,653,590, and U.S. Pat. No. 5,762,541.

Since root canals are seldom straight, often having bends and twists, at least some endodontic files are advantageously flexible. Currently preferred materials of construction include stainless steel, and more recently, nickel-titanium (Ni—Ti) alloys. Such materials, especially Ni—Ti alloys, exhibit good flexibility, resilience and strength, and are not likely to fail during use. Flexibility and strength are important to avoid file breakage during the cleaning process.

Endodontic instruments may be designed to be manually manipulated or to be fitted to a powered handpiece that provides rotation of the file during its use. An endodontic instrument that is intended for hand use is typically provided with an enlarged diameter plastic handle attached to the proximal end of the instrument, configured for easy manipulation between the thumb and forefinger of the dental practitioner. An instrument intended for use with a powered handpiece has a stem at the instrument proximal end configured to be removably received within a chuck of the powered handpiece, by which the instrument may then be rotated as desired by a dental practitioner.

One current method of manufacturing existing endodontic files is by a grinding operation. In the grinding operation, a metallic (typically a titanium alloy) rod is advanced past a rotating grinding wheel at a relatively slow feed rate. The depth of cut may be varied along the length of the rod in order to produce a tapered endodontic file. Such a method is disclosed in U.S. Pat. No. 5,762,541.

Tapering and grinding the rod in this way requires complex and precise machining equipment with many moving parts to perform the grinding, rotating, and tapering of the rod. The method is quite complex and relatively expensive.

It would be an improvement in the art to provide an alternative method of manufacture capable of producing tapered endodontic instruments at a reasonable cost using machinery of reduced complexity.

BRIEF SUMMARY OF THE INVENTION

The present invention provides a method for manufacturing endodontic instruments. According to one embodiment, the invention involves the steps of (a) providing a metallic rod having a cutting portion with a polygonal cross section; (b) torsioning the rod so as to form helical cutting surfaces in the cutting portion of the metallic rod; and (c) chemically milling the cutting portion of the rod so as to form a cutting portion having a desired taper and/or so as to further sharpen the cutting surfaces.

The metallic rod may have any of various polygonal cross sections, such as triangular, square, or any of various regular or irregular shapes bounded by straight or curved sides. The cutting portion of the metallic rod is typically torsioned, which may be accomplished by holding one end of the cutting portion stationary while twisting the opposite end. Torsioning the rod causes the apices of the polygon to be twisted to form helical cutting surfaces along the cutting portion of the rod.

It will be appreciated that cutting surfaces can be formed in any manner known in the art. For example, a non-tapered file (or even a file having an initial taper) can be formed by any known method (e.g., grinding, cutting, particulate blasting, machining, laser micromachining, and the like) and then tapered using a chemical milling process to yield an endodontic instrument having a desired final taper. The chemical milling process also tends to sharpen the cutting surface. In the case of files formed by grinding or machining, chemical milling can also create a more even and contiguous surface by subtracting microfissures or cracks that can propagate and promote breakage. Chemical milling thus yields an endodontic file less prone and more resistant to breakage.

Once an intermediate instrument having a cutting surface is formed, the cutting portion of the intermediate instrument is tapered by a chemical milling process. In one embodiment, the intermediate instrument is placed in a chemical bath. The bath composition may include hydrofluoric acid, nitric acid, water and a wetting agent. The longer the time that any specific portion of the file is in contact with the chemical milling solution, the greater will be the amount of metallic material stripped or removed from that portion. In one embodiment, at least the cutting portion of the metallic rod is submerged within the chemical milling composition and allowed to soak in the chemical milling solution. Allowing a soak time allows the chemical milling solution to remove the outer metal oxide layers of the cutting portion. Afterwards, the cutting portion is progressively withdrawn at a predetermined rate so as to result in a tapered cutting portion having a desired angle of taper. In another embodiment, no soak time is required, and the cutting portion may be progressively inserted and/or progressively withdrawn from the chemical milling solution, so as to result in a tapered cutting portion having a desired angle of taper.

Specific soak times (optional) and rates of insertion and/or withdrawal from the chemical milling composition depend on the chemical milling composition used, what type of material the intermediate file is formed from, the starting thickness of the rod, and the taper to be realized. When used, soak times preferably range from about 1 minute to about 1 hour, more preferably from about 3 minutes to about 30 minutes, and most preferably from about 5 minutes to about 20 minutes. Soaking removes the metal oxide layers that may otherwise interfere with the formation of a smooth taper.

Preferred rates of insertion and/or withdrawal range from about 0.1 mm per minute to about 6 mm per minute, more preferably from about 0.5 mm per minute to about 3 mm per minute and most preferably about 0.8 mm per minute to about 1.2 mm per minute.

According to one embodiment, the chemical milling process can optionally be enhanced by passing a weak electric current through the endodontic file and/or chemical bath. While superficially related to "electro-polishing", chemical milling with optional electric current is believed to increase the rate of chemical milling by increasing the temperature rather than through reverse electroplating per se.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the invention endodontic instruments and manufacturing methods will now be provided, with specific reference to figures illustrating preferred embodiments of the invention. It will be appreciated that like structures will be provided with like reference designations. To provide context for interpreting the scope of the invention, certain terms used throughout the application will now be defined.

As used herein, the terms endodontic "instrument" and endodontic "instruments" refer to endodontic files and other instruments used in a root canal or other endodontic procedure. The terms "intermediate file" or "intermediate instruments" shall refer to metallic substrates before being chemically milled.

As used herein, the terms "polygon" and "polygonal" refer to a shape that is closed and bounded by straight or curved sides. Non-limiting examples include a triangle, a square, a rectangle, a pentagon, a spherical triangle, or any other of various regular or irregular shapes, including, but not limited to, the shapes disclosed herein, as exemplified in FIGS. 3A-3G.

As used herein, the terms "chemical milling," "stripping" and "etching" refer to a procedure whereby a material is worked or shaped by exposure to a chemical bath. While exposed to the chemical bath, the shaping occurs as bits of material are "stripped" or "etched" off because of the chemical action of the bath. "Chemical milling" may involve passing an electric current through the endodontic instruments and/or the chemical bath in order to enhance the stripping process.

As used herein, the term "soak time" refers to the amount of time that the metallic rod is exposed to the chemical milling composition of the chemical bath while in a stationary state. Soaking the metallic rod is optional and removes metal oxide layers that may otherwise interfere with the formation of a smooth taper.

I. Exemplary Endodontic Instruments

Figure 1:
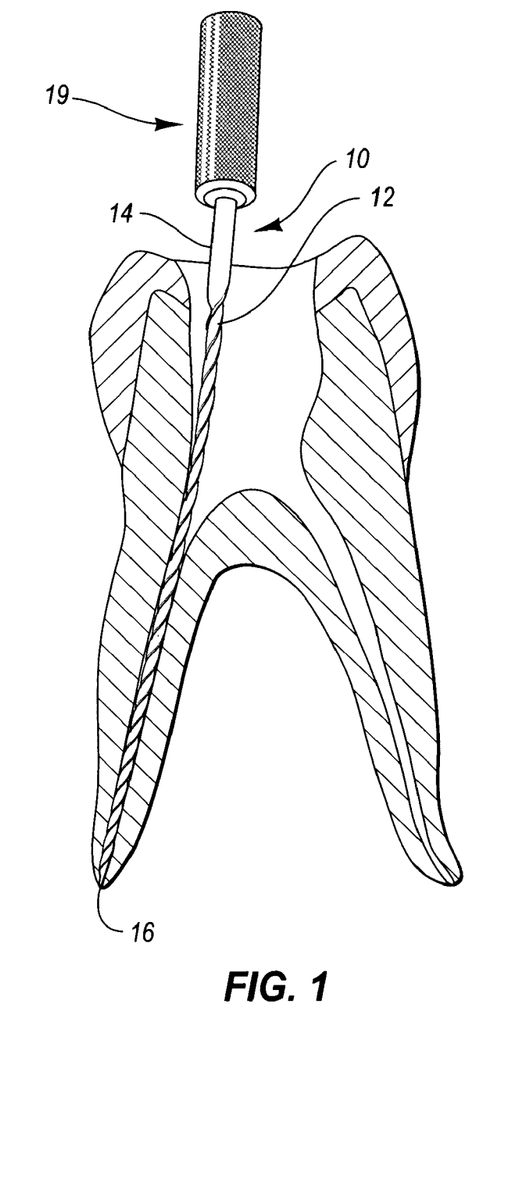
FIG. 1 is a cross sectional view of a tooth having two roots, with an endodontic instrument being positioned in one of the roots.
Figure 2:
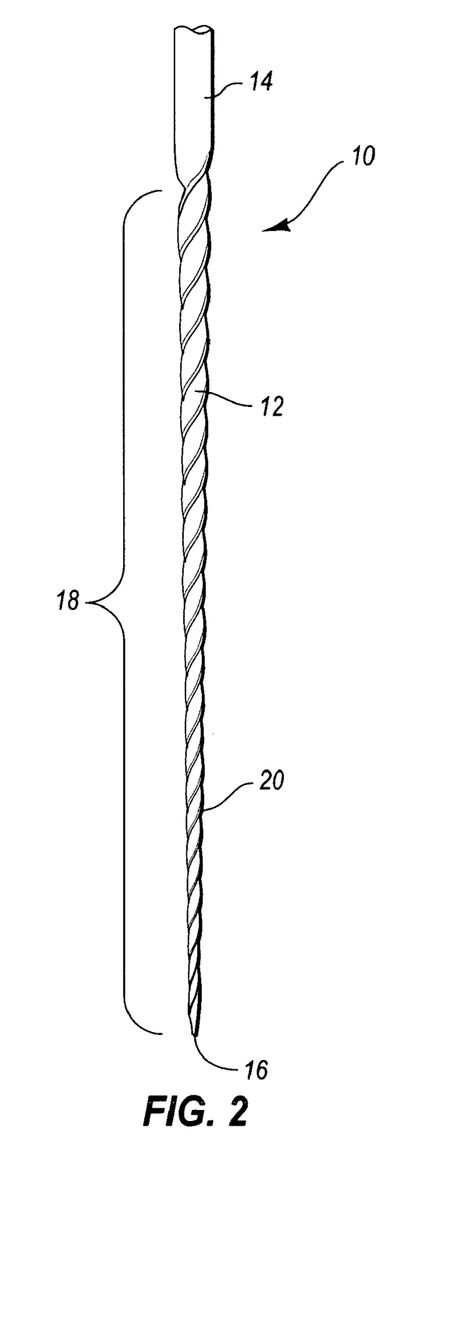
FIG. 2 is a perspective view of the cutting portion of an exemplary endodontic instrument.

Referring to FIGS. 1 and 2, an endodontic instrument 10 is illustrated which comprises a metallic rod 12 having a proximal end 14, and a distal end 16. At least a portion of the metallic rod 12 comprises a cutting portion 18 of the endodontic instrument, which is disposed between the proximal end 14 and the distal end 16. In this embodiment, the cutting portion 18 includes at least one helical cutting edge 20 that extends helically around metallic rod 12. A handle 19 may be provided adjacent the proximal end 14 of the metallic rod 12 in order to facilitate gripping of the endodontic instrument 10 by the user or a dental hand piece (e.g., a reciprocating hand piece).

The cutting portion 18 is preferably tapered between the proximal end 14 and the distal end 16, with decreasing diameter or width toward the distal end 16. The taper may be continuous or incremental (i.e. stair stepped). The taper may be any amount desired, but is preferably between about 0.02 mm/mm and about 0.06 mm/mm. The specific taper of any instrument will depend on the intended use and dental practitioner preference. For example, a taper of 0.0225 mm/mm may be preferred when preparing a root canal that is to receive a gutta percha cone having a taper of about 0.02 mm/mm.

The cutting portion 18 may have a length of about 2 mm up to the full length of the rod 12, which may be as much as about 30 mm or more. In the illustrated embodiment, the cutting portion 18 has a length sufficient to extend substantially the full depth of a tooth root canal as illustrated in FIG. 1. It will be appreciated, however, that the cutting portion may terminate before reaching the tip 16, as in a coronal file, or comprise a small length near the tip 16 as in an apical file.

Figure 3A:
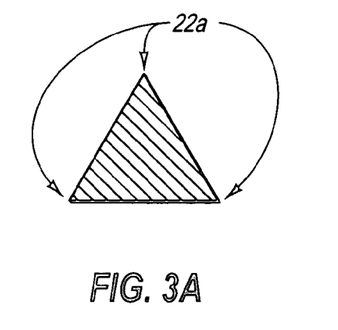
FIGS. 3A-3G illustrate several different polygonal transverse cross sections through several exemplary endodontic instruments manufactured according to the method of the present invention.

The cross sectional configuration of the cutting portion 18 of the instrument illustrated in FIGS. 1 and 2 is triangular and is composed of three linear sides, as best seen in FIG. 3A. The apices 22a of the triangle form cutting edges 20. The cutting portion 18 may be of any polygonal cross section such that when the rod is torsioned, cutting edges 20 are formed.

Figure 3B:
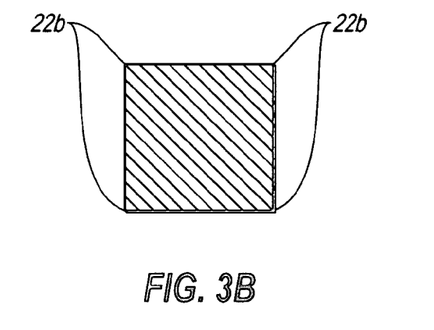
Figure 3C:
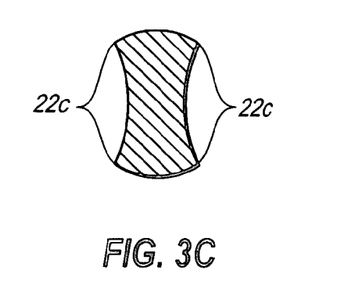

Several non-limiting examples of suitable polygonal cross sections are illustrated in FIGS. 3A-3G. FIG. 3A illustrates a triangular cross section in which apices 22a form three cutting edges 20. FIG. 3B illustrates a square cross section in which line intersections 22b form four cutting edges. FIG. 3C illustrates a cross section bounded by four curved sides, two of which are concave and two of which are convex. The intersections 22c between the convex and concave sides form four cutting edges.

Figure 3D:
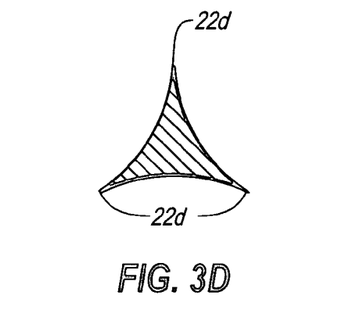
Figure 3E:
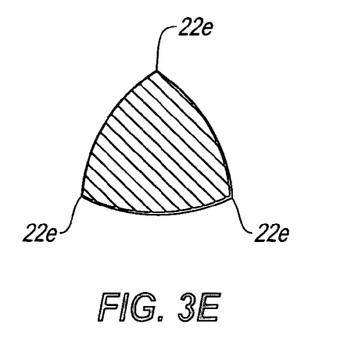

FIGS. 3D and 3E illustrate alternative spherical triangular cross sections, with the triangle cross section of FIG. 3D having concave surfaces between the apices 22d of the triangle and with the triangle cross section of FIG. 3E having convex surfaces between apices 22e of the triangle.

Figure 3F:
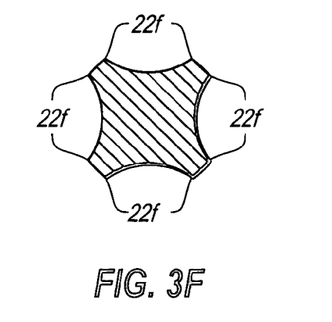
Figure 3G:
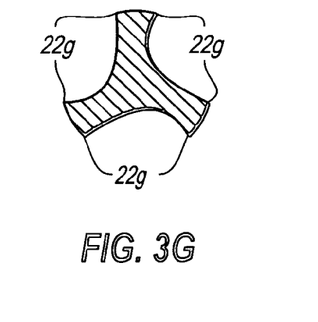

FIG. 3F illustrates a cross section bounded by a combination of four concavely curved sides separated by four straight sides. The intersection 22f between the straight and curved sides form eight cutting edges. FIG. 3G illustrates a cross section of an irregular polygon bounded by three concavely curved sides separated by three convexly curved sides. The intersections 22g between the six curved sides yield six cutting surfaces.

When torsioned, the apices or edges 22a-g of the various cross sections form helical cutting edges 20.

II. Method of Manufacture

FIGS. 4, 5A, 5B and 6A-6E illustrate exemplary embodiments of methods of manufacturing endodontic instruments according to the present invention. As will be further described below, the method involves a unique process which has been found to efficiently produce endodontic instruments of the type described, from a metallic wire. The metallic wire may be formed of any suitable metallic material, for example stainless steel, a nickel-titanium alloy (Ni—Ti), nickel-titanium-chromium alloy, a nickel-titanium-copper alloy, a nickel-titanium-niobium alloy, or any other superelastic metallic material. Although any suitable metallic material may be used, nickel-titanium alloys are preferred because they are strong yet flexible and resilient. The Ni—Ti alloy preferably has a titanium content in a range of about 20% to about 80%, more preferably in a range of about 30% to about 70%, and most preferably in a range of about 40% to about 60%. In one embodiment, the balance of the alloy may comprise nickel and small amounts of other ingredients which do not adversely affect the suitability of the material for use as an endodontic instrument.

The wire from which the endodontic instrument is to be manufactured may be supplied already drawn in a selected polygonal cross sectional shape. Alternatively, the wire may be supplied in a circular cross section and then shaped to the desired cross section by processes known to those of skill in the art. With regard to wire thickness, endodontic instruments are sized in accordance with established standards, which range from a thickness at the distal end 16 of 1.4 mm (size 140) to a thickness at the distal end 16 of 0.06 mm (size 06).

Figure 4:
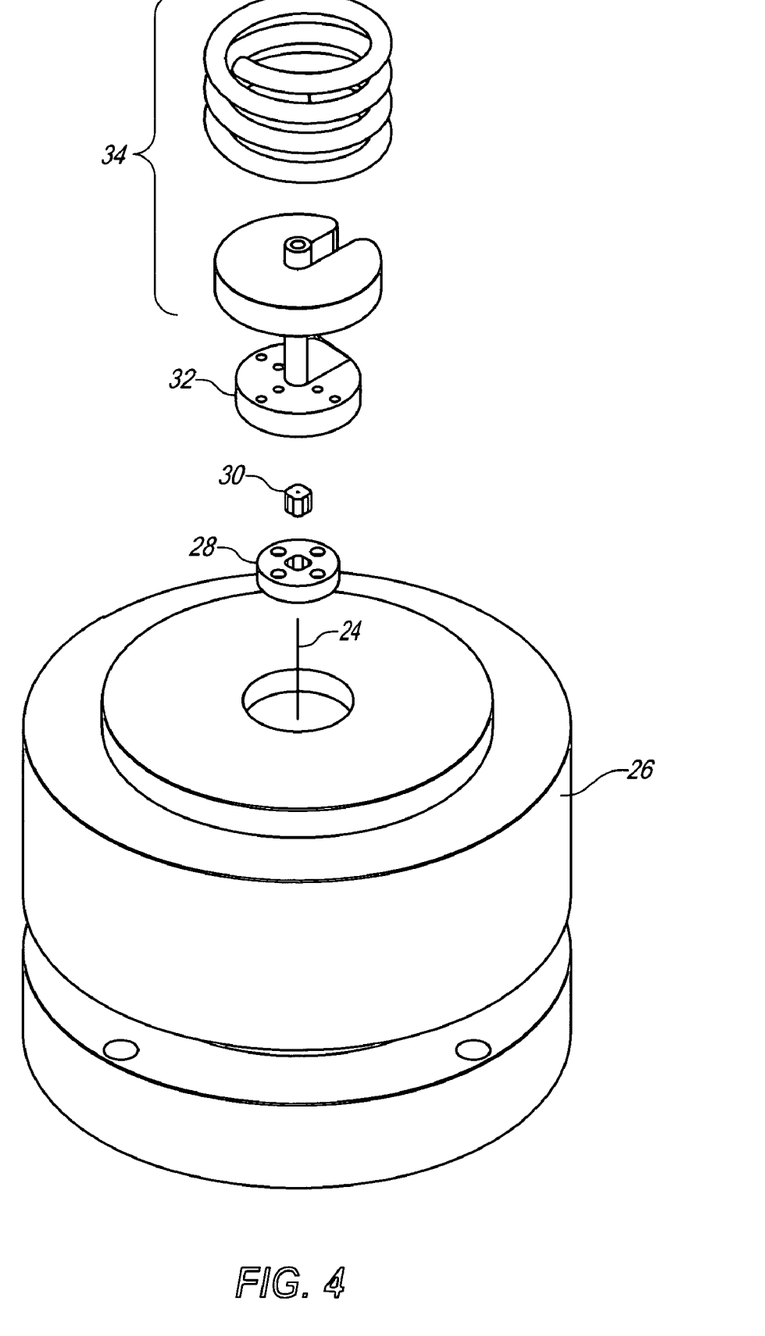
FIG. 4 is an exploded view of an apparatus for torsioning metallic rods for manufacturing endodontic instruments according to the present invention.

FIG. 4 depicts an exemplary apparatus (in exploded view) for performing the first steps of an exemplary method of manufacture according to one embodiment. The exemplary apparatus includes a collet 26, housing cap 28, insert 30, insert housing 32, and coil assembly 34. The continuous wire is first cut to a desired length. The wire length 24 is positioned to extend out of collet 26, which may be of well known construction. Wire length 24 extends out collet 26 and into insert 30, which is nearly surrounded by housing cap 28. In order to receive wire 24, insert 30 includes a passage through its center having the same cross section shape as wire 24. The passage is slightly larger than wire 24 so as to allow clearance for the wire 24 to be received within insert 30. The ends of the passage may be flared so as to facilitate inserting the wire 24 through the passage.

Insert 30 is formed of a hard material, preferably a ceramic such as cermet. The insert 30 and housing cap 28 are received within insert housing 32. Coil assembly 34 (for heating) surrounds the insert housing and insert. The wire 24 is heated, and then torsioned. Torsion is accomplished by turning and retracting the collet 26.

The wire 24 may be heated by any known method prior to torsioning. Examples of suitable heating methods include electrical resistive heating, convection heating, direct heating by a torch, or RF high frequency induction heating. RF high frequency induction heating is a preferred heating method. In RF high frequency induction heating, the wire 24 is heated while positioned through coil assembly 34 into which an electrical current is fed. The electrical current and coil assembly 34 create a heating field that may be focused on the wire 24 as it is positioned through the coil assembly 34. Heating wire 24 makes it easier to subsequently torsion the wire.

In order to avoid oxidation of the metal wire 24 while heating, when possible, the heating is preferably performed in an inert environment, such as under a noble gas environment. Examples of inert gases that may be used include, but are not limited to, helium, argon and even nitrogen in those cases where the heated metal does not adversely react with nitrogen to form a brittle product. Because allows of titanium can react with nitrogen to form titanium nitride, which is brittle, it may not be advantageous to use nitrogen gas when manufacturing an endodontic file from titanium alloys. Nitrogen works well with other metals, such as stainless steel.

Insert 30 and collet 26 function together to torsion wire 24. While both ends of the wire 24 are gripped, collet 26 turns, which twists the wire 24 about its longitudinal axis. This causes the apices or intersections 22 of the polygonal cross section of the wire 24 to form helical cutting edges 20 as described above with respect to FIGS. 1 and 2. Collet 26 is retracted either during or after turning, removing wire 24 from insert 30.

Figure 5A:
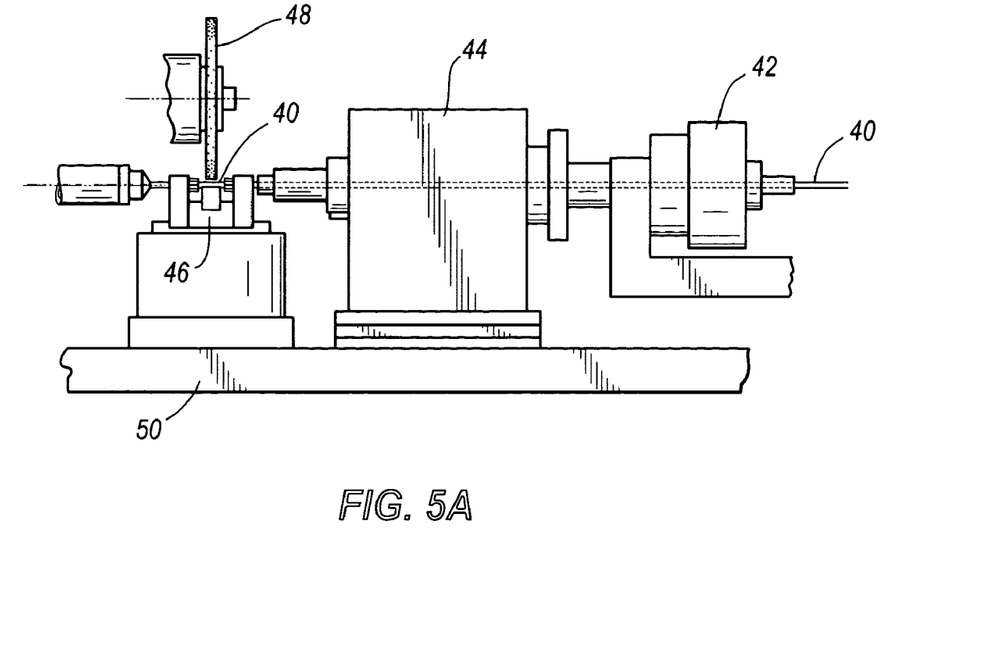
FIGS. 5A and 5B depict a machining apparatus used to machine or grind a cutting edge into an endodontic file.
Figure 5B:
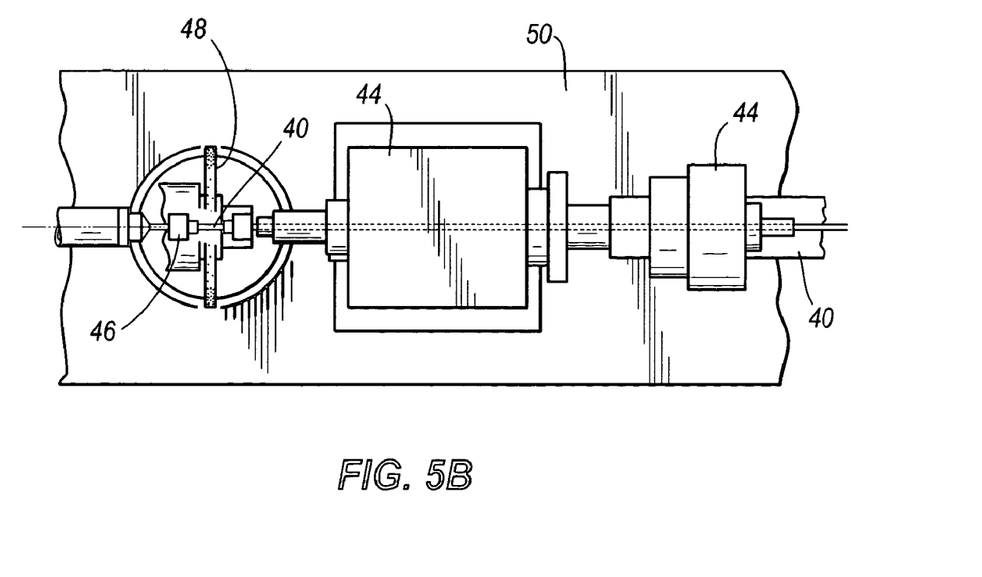

FIGS. 5A and 5B depict an alternative embodiment for forming a cutting edge or surface of an endodontic instrument prior to chemical milling, which produces a desired taper and/or further sharpens the cutting edge. In accordance with this embodiment, a metallic rod 40, which may be continuous, is positioned so as to extend through an axial feed block 42 and an indexing block 44 of conventional construction. A work-holding fixture 46 is positioned to support the forward end of the rod 40 adjacent to the periphery of a rotating grinding wheel 48. The two blocks 42, 44 are then advanced so that the rod 40 is axially moved past the rotating grinding wheel 48 at a slow feed rate of between about 3-8 inches per minute. Concurrently with this axial movement, the indexing block 44 serves to slowly rotate the rod 40 about its axis at a controlled speed, which causes the ground surface of the rod 40 to assume a helical configuration.

The rod 40 preferable moves past the grinding wheel 48 only once for each ground cutting edge. Thus the rod 40 is positioned with respect to the grinding wheel 48 such that the full depth of the cut is removed in a single pass. The grinding wheel 48 preferably removes at least about 25% of the diameter of the rod 40 at the point of maximum removal, which is along a diameter which extends perpendicular to the cutting edge being formed.

The grinding wheel 48 is rotated at a relatively slow surface speed of not more than about 3,000 feet per minute, and preferably not more than about 2,200 feet per minute. Further, the grinding wheel 48 is composed of a relatively fine grit (e.g., greater than about 200, and preferably about 220 grit). The grinding wheel 48 is oriented to rotate about an axis generally parallel to the axis of the advancing rod 40, in order for the grinding wheel 48 to thereby form a generally flat grinding surface. Also, by reason of the slow rotation of the rod 40 about its axis, this flat surface assumes a helical configuration. If the instrument is to have a tapered working length prior to chemical milling, the axis of the index block 44 is slightly inclined with respect to the rotational axis of the grinding wheel 48 so as to provide a controlled and variable depth of cut along the working length.

When the rod 40 has advanced past the rotating wheel 48 a distance sufficient to form a first cutting surface along the desired working length, the table 50 supporting the feed block 42, the index block 44, and the fixture 46 is moved laterally, then axially rearwardly, and then laterally back to its original position. Concurrently, the rod 40 is rotatably indexed about its axis. The angular extent of this rod indexing will depend upon the number of cutting surfaces desired on the finished instrument, and where three surfaces are to be formed, the rod is indexed 120°. The rod is then axially advanced while being slowly rotated, so as to form a second cutting surface. The table 50 is then again moved laterally and rearwardly in the manner described above, and the rod 40 is rotatably indexed another 120°. The grinding process is then repeated to form the third cutting surface of the instrument.

The rod 40 may then be severed by conventional techniques, such as by axially advancing the rod 40 and then moving the grinding wheel laterally through the rod 40. The severed rod 40 is then further processed by chemical milling described more fully below. A more detailed description of a machining or grinding process is set forth in U.S. Pat. No. 5,762,541, which is incorporated by reference with respect to forming a cutting edge by machining and grinding, but which is modified and improved according to the invention so as to include the chemical milling process.

Once a length of wire 24 has been cut and torsioned to form a metallic rod 12 (or a rod 40 has been machined, ground or otherwise processed to yield a desired intermediate having a cutting edge or surface), the rod is ready to be chemically milled. Although the current example involves chemically milling the rod after torsioning, cutting, machining, grinding, grit blasting and the like, the order is not critical, and the torsioning and/or other process could be performed after chemical milling. In either case, the cutting portion 18 is tapered and/or sharpened by chemically milling at least a portion of the cutting portion 18 of the metallic rod 12.

The cutting portion 18 of rod 12 is chemically milled by placing the cutting portion 18 into a bath containing a chemical milling composition. The composition may contain an acid, water, and a wetting agent. Suitable acids include hydrofluoric acid and nitric acid. One currently preferred composition includes about 10% hydrofluoric acid, about 20% nitric acid, about 0.8% Dapco 6001, a wetting agent, and the balance water. Percentages are given as percent by volume.

It is preferable to maintain the chemical milling solution at a temperature between about 15° and about 105° C., more preferably about 25° and about 90° C., and most preferably about 35° and about 65° C. In addition, it is preferable to stir the chemical milling solution. Suitable stirring rates include about 1 to 1200 RPM.

The cutting portion 18 of each rod 12 can be tapered by progressively inserting and/or withdrawing the cutting portion 18 from the chemical milling composition 36. FIGS. 5A-5E illustrate tapering by progressively withdrawing the cutting portion 18. The rate at which the rod 12 is inserted and/or withdrawn from the composition 36 will depend on the chemical milling composition 36 used, what type of material the rod 12 is formed of, the starting thickness of the rod 12, and the taper to be realized. Slower rates of insertion and/or withdrawal result in longer treatment times, which generally result in greater tapering of the cutting portion 18.

In one embodiment, it may be desirable to soak at least said cutting portion in said chemical milling composition for a predetermined soak time prior to withdrawal from the chemical milling composition. When used, preferably soak times are from between about 1 minute and about 60 minutes, more preferably 3 minutes to about 30 minutes, and most preferably about 5 minutes to about 20 minutes. Soaking strips off the outer metal oxide layers, which may result in a smoother taper.

The amount of metallic material stripped away by the milling composition is proportional to the treatment time of any specific portion of the metallic rod. In order to strip or etch more metal from the distal end 16 of the endodontic file 10, the distal end 16 of the endodontic instrument 10 will be submerged longer in the composition 36 than the rest of the cutting portion 18 of rod 12. The cutting portion 18 of rod 12 is progressively inserted and/or withdrawn from the composition 36 at a predetermined rate, resulting in a metallic rod with a tapered cutting portion 18.

The metallic rod 12 may be inserted and/or withdrawn at any desired rate, although it is preferable to insert and/or withdraw the rod 12 at a rate of between about 0.1 mm per minute to about 6 mm per minute, more preferably about 0.5 mm per minute to about 3 mm per minute and most preferably about 0.8 mm per minute to about 1.2 mm per minute. The specific rate of insertion and/or withdrawal depends on the actual chemical milling composition 36 used, what type of material the rod 12 is formed of, the starting thickness of the rod 12, and the taper to be realized. One of ordinary skill will be able to select a rate that will yield a desired taper for a given metallic rod.

The metallic rod 12 is preferably inserted and/or withdrawn continuously from the chemical milling composition 36 so as to form a smooth taper, although the rod 12 could alternately be inserted and/or withdrawn incrementally from the chemical milling composition. Incremental insertion and/or withdrawal results in a stepped taper rather than a smooth taper, which may be desirable in some applications.

Figure 6A:
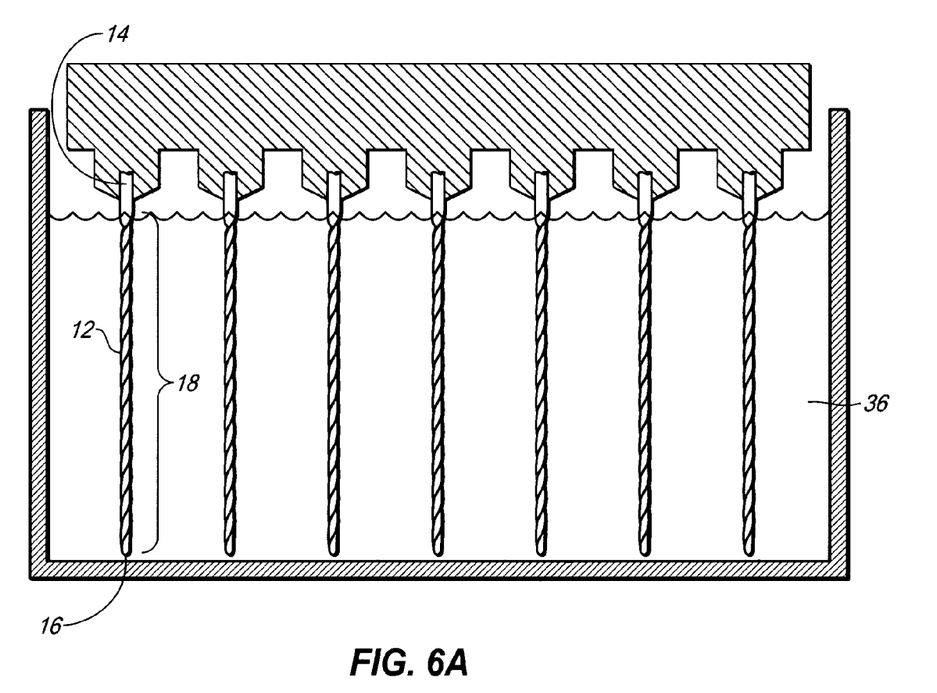
FIGS. 6A-6E depict exemplary metallic rods being chemically milled to taper the cutting portions of the metallic rods.
Figure 6B:
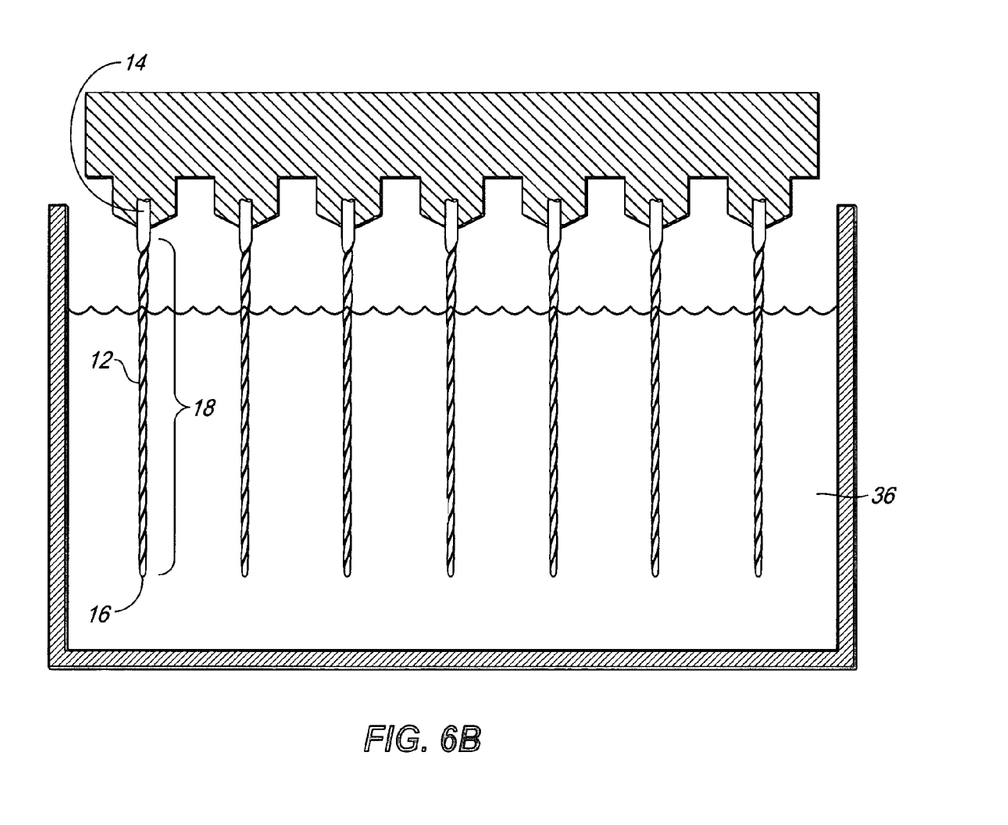
Figure 6C:
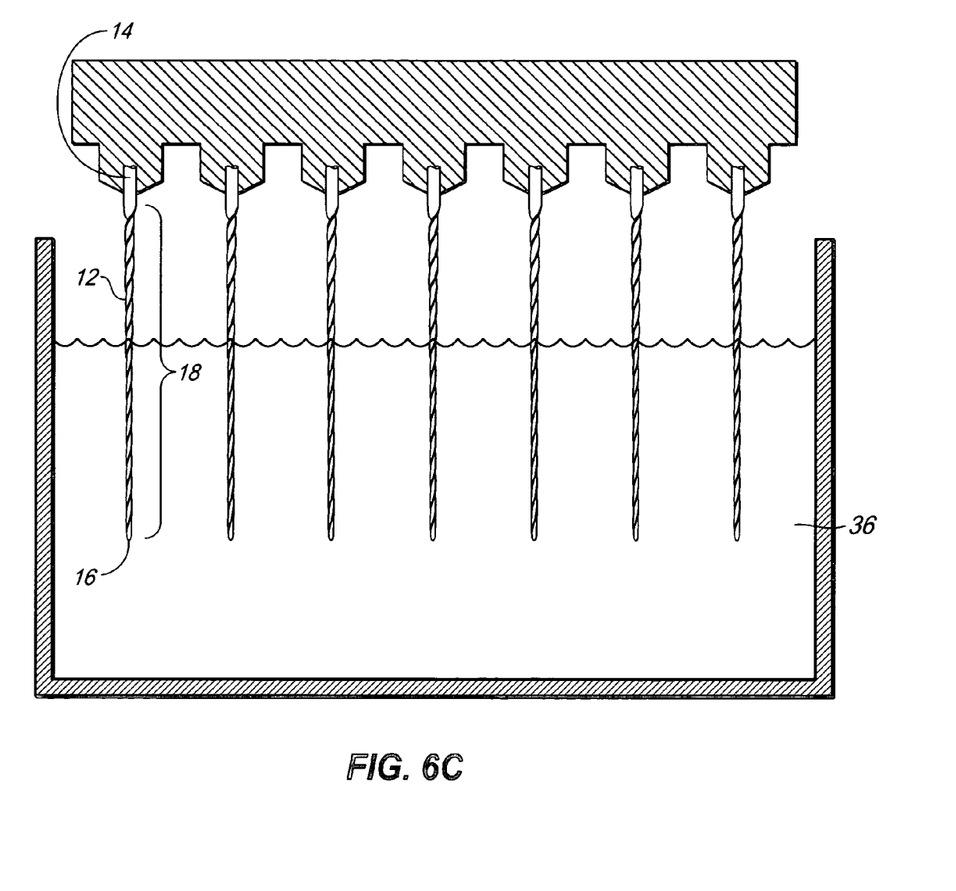
Figure 6D:
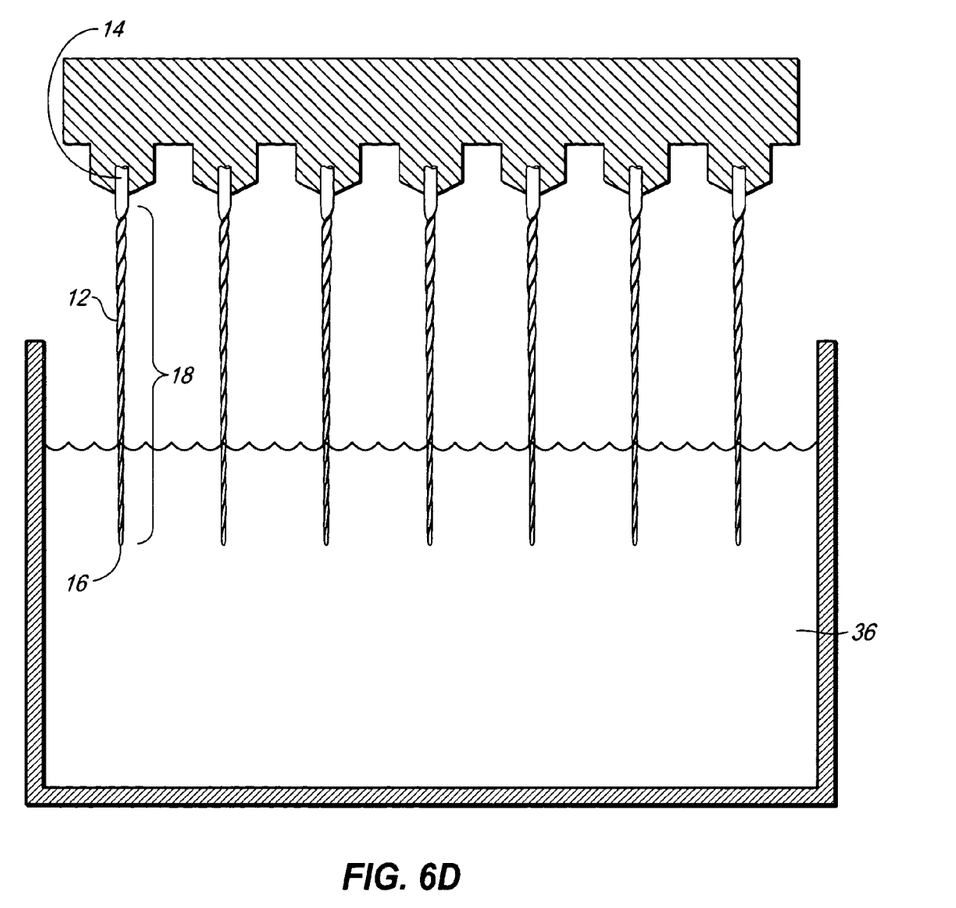
Figure 6E:
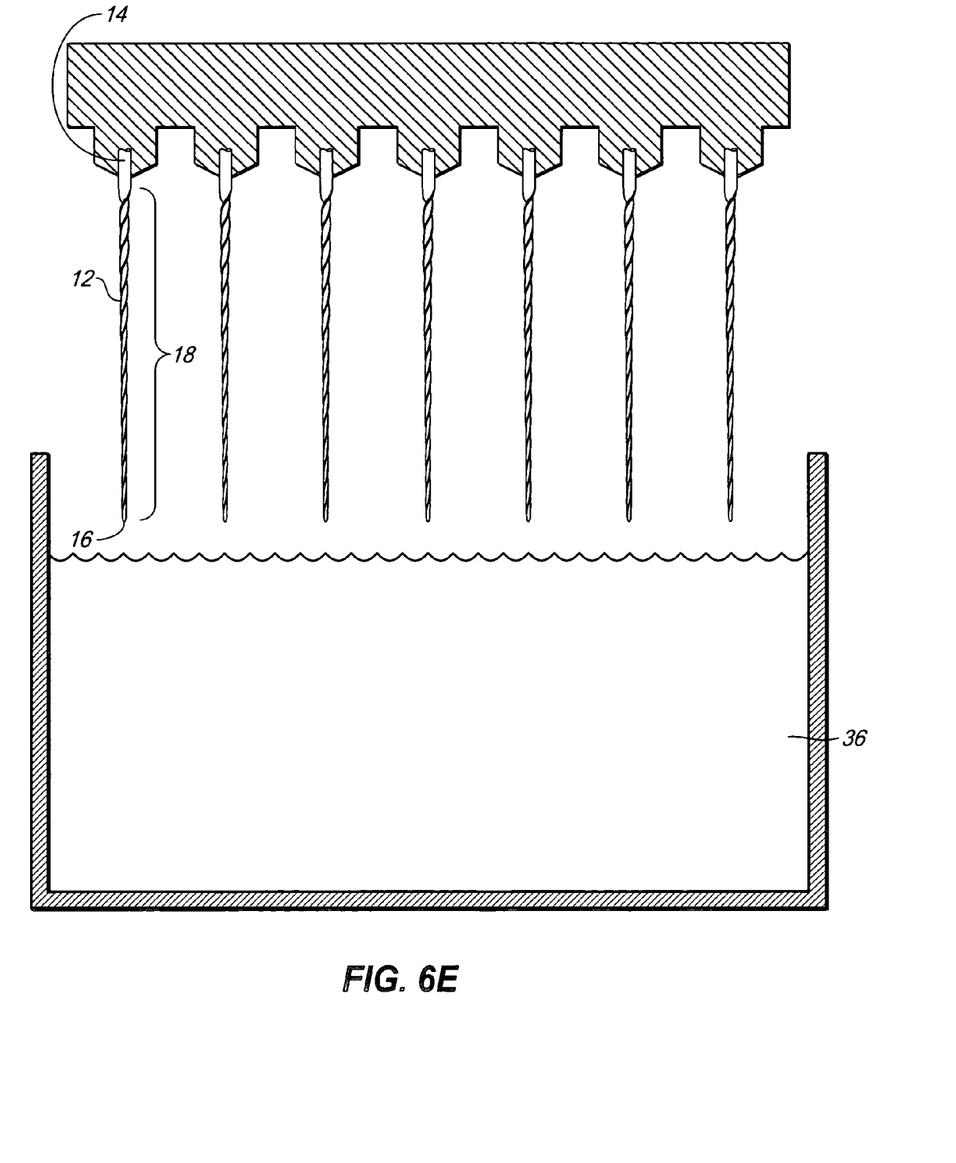

FIGS. 6A-6E illustrate different stages during the chemical milling process where the rod 12 is progressively withdrawn from the milling composition 36. FIG. 6A illustrates a state at the beginning of the chemical milling process where the entire cutting portion 18 of each metallic rod 12 is submerged in the composition 36. FIG. 6B illustrates an intermediate stage during the chemical milling process where the cutting portion 18 of rod 12 has been partially withdrawn from milling composition 36. FIG. 6C illustrates a more advanced intermediate stage where cutting portion 18 has been further withdrawn, while FIG. 6D illustrates a yet more advanced intermediate stage where cutting portion 18 has been almost completely withdrawn. FIG. 6E illustrates a stage where the cutting portion 18 has been completely withdrawn from milling composition 36.

Figure 7A:
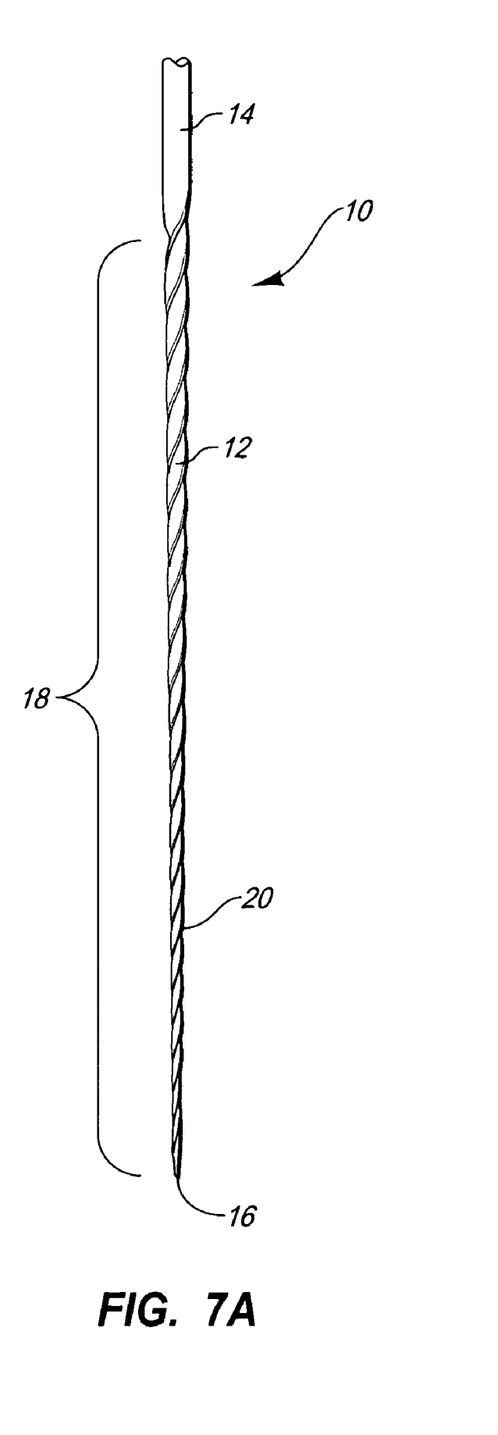
FIGS. 7A and 7B depict exemplary tapered metallic rods.
Figure 7B:
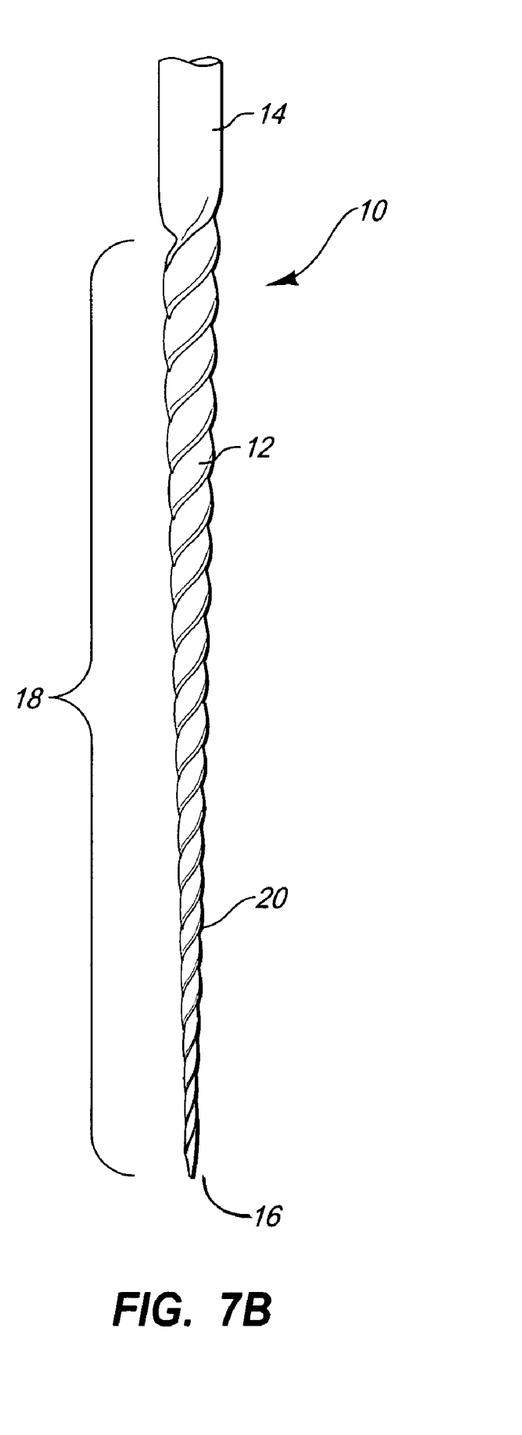

FIGS. 7A-7B illustrate exemplary endodontic instruments 10 having continuous tapered cutting portions 18. The instrument illustrated in FIG. 7A includes a taper of about 0.02 mm/mm while that illustrated in FIG. 7B includes a taper of about 0.06 mm/mm.

In some cases, the chemical milling process results in a sharper cutting edge as layers of metal are removed adjacent to the cutting edge. In some cases, the chemical milling process can be used solely to sharpen the cutting edge rather than form a tapered instrument. In such cases, the entire length of the instrument may be submerged in the chemical bath for approximately the same amount of time. In some cases, the instrument may already be tapered before chemical milling (e.g., by grinding, cutting or machining). In the case of instruments formed by grinding or machining, chemical milling can be used to remove microfissures or cracks caused by grinding that can easily propagate during use, causing fracture of the file in a person's root canal. Chemical milling can remove such cracks, yielding a superior contiguous surface and a file that is more resistant to breakage during use.

The chemical milling process may optionally be enhanced by passing an electrical current through the endodontic instrument and/or the chemical bath. In many cases, it will be preferable to use a weak electric current in order to merely enhance chemical milling rather than initiate electro-polishing or reverse electroplating. Passing a relatively weak electric current through the endodontic instrument and/or chemical bath is believed to enhance the chemical milling process by increasing the temperature at which the chemical milling process occurs. For example, increasing the temperature of an aqueous acid in the vicinity of the cutting edge may increase the rate at which the acid is able to strip layers of metal atoms from the endodontic instrument. Regardless of whether or not an electric current is passed through the endodontic instrument and/or chemical bath, the use of a chemical milling solution of the type disclosed herein will generally result in "chemical milling".

After chemical milling, the rod 12 is then further processed in a conventional manner to form the completed instrument as illustrated for example in FIG. 1 (e.g. fitting a handle or stem 19 to proximal end 14, optionally surface finishing the rod 12, etc). The process as described and claimed has been found to produce inexpensive high quality endodontic instruments. In addition, with at least some polygonal cross sections, tapering by chemical milling has been found to result in cutting surfaces which sharpen as they are chemically milled. The process is suitable for commercial application to manufacture as few or as many instruments at a time as desired, and does not require the complex mechanical milling machinery required by existing manufacturing methods.

It will be appreciated that the cutting surfaces or edges of the endodontic instruments may be formed by other means known in the art instead of torsioning. For example, they may be formed by cutting, grinding, grit blasting, machining, laser micromachining, and the like.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A method of manufacturing an endodontic instrument for use in performing an endodontic procedure, comprising:
   (a) providing an intermediate instrument comprised of a metal and having a cutting portion;
   (b) providing a chemical milling composition that chemically strips metal from a surface of a metallic substrate as a result of chemical action of the chemical milling composition; and
   (c) chemically milling at least a portion of said cutting portion by contacting at least a portion of said cutting portion with said chemical milling composition so as to chemically strip metal from an entire surface of the portion of said cutting portion in contact with said chemical milling composition so as to yield an endodontic instrument having a desired taper and/or cutting edges having a desired degree of sharpness and/or a more contiguous surface with fewer microfissures or cracks.

2. The method as recited in claim 1, wherein (c) is performed by progressively inserting and/or withdrawing said cutting portion into and/or from said chemical milling composition at a predetermined rate.

3. The method as recited in claim 2, further comprising soaking at least said cutting portion in said chemical milling composition for a predetermined soak time of between about 1 minute and about 60 minutes.

4. The method as recited in claim 2, wherein said cutting portion of said rod is inserted into and/or withdrawn from said chemical milling composition at a rate of between about 0.1 mm per minute and about 6 mm per minute.

5. The method as recited in claim 2, wherein said cutting portion of said rod is inserted into and/or withdrawn from said chemical milling composition at a rate of between about 0.5 mm per minute and about 3 mm per minute.

6. The method as recited in claim 2, wherein said cutting portion of said rod is inserted into and/or withdrawn from said chemical milling composition at a rate of between about 0.8 mm per minute and about 1.2 mm per minute.

7. The method as recited in claim 1, wherein said chemical milling composition is acidic.

8. The method as recited in claim 7, wherein said chemical milling composition comprises hydrofluoric acid, nitric acid, water, and a wetting agent.

9. The method as recited in claim 1, wherein at least a portion of said cutting portion is formed by machining or grinding a metallic rod so as to form said cutting edges in said cutting portion.

10. The method as recited in claim 1, wherein at least a portion of said cutting portion is formed by at least one of cutting, grinding, laser micromachining, machining, or grit blasting.

11. The method as recited in claim 1, wherein at least a portion of said cutting portion is formed by torsioning a metallic rod having a polygonal cross section so as to form helical cutting edges in said cutting portion.

12. The method as recited in claim 1, wherein (c) produces a cutting portion taper of between about 0.02 mm/mm and about 0.06 mm/mm.

13. The method as recited in claim 1, wherein (c) sharpens said cutting edges as they are chemically milled.

14. The method as recited in claim 1, wherein (c) does not result in significant tapering of said endodontic instrument.

15. The method as recited in claim 1, wherein said intermediate instrument having a cutting portion is tapered prior to (c).

16. The method as recited in claim 1, wherein (c) further comprises passing an electric current through at least one of said intermediate instrument or said chemical milling composition.

17. The method as recited in claim 1, wherein (c) comprises chemically milling a plurality of intermediate instruments simultaneously.

18. A method of manufacturing an endodontic instrument adapted for use in performing an endodontic procedure, comprising:
   (a) providing a metallic rod;
   (b) forming said rod into an intermediate endodontic instrument having a cutting portion comprised of at least one helical cutting edge; and
   (c) chemically milling at least a portion of said cutting portion of said intermediate endodontic instrument by contacting at least a portion of said cutting portion with a chemical milling composition in order to chemically strip metal from an entire surface of the portion of said cutting portion in contact with said chemical milling composition so as to sharpen said at least one helical cutting edge and/or taper said cutting portion and/or remove microfissures or cracks in said cutting portion.

19. The method as recited in claim 18, wherein said rod is formed of a nickel-titanium alloy.

20. A method of manufacturing an endodontic instrument adapted for use in performing an endodontic procedure, comprising:
   (a) providing a metallic rod having a polygonal cross section;
   (b) torsioning, grinding and/or machining said rod so as to form an intermediate endodontic instrument having a cutting portion comprised of at least one helical cutting edge in said cutting portion; and
   (c) chemically milling at least a portion of said cutting portion of said intermediate endodontic instrument by contacting at least a portion of said cuffing portion with a chemical milling composition in order to chemically strip metal from an entire surface of the portion of said cutting portion in contact with said chemical milling composition so as to sharpen said at least one helical cutting edge and/or taper said cutting portion and/or remove microfissures or cracks in said cutting portion.

* * * * *

UNITED STATES PATENT AND TRADEMARK OFFICE
CERTIFICATE OF CORRECTION

PATENT NO. : 7,398,598 B2  Page 1 of 1
APPLICATION NO. : 10/991178
DATED : July 15, 2008
INVENTOR(S) : Lewis et al.

It is certified that error appears in the above-identified patent and that said Letters Patent is hereby corrected as shown below:

Column 6
Lines 4 and 6, change "than wire" to --than the wire--
Line 10, change "Insert" to --The insert--
Line 34, change "allows" to --alloys--
Line 63, change "preferable" to --preferably--

Column 7
Line 52, change "process" to --processes--
Line 56, change "of rod" to --of the rod--

Column 9
Line 17, change "causing fractue of file" to --causing the file to fracture--

Signed and Sealed this

Twenty-first Day of July, 2009

JOHN DOLL
*Acting Director of the United States Patent and Trademark Office*